United States Patent [19]
Owens

[11] Patent Number: 6,092,536
[45] Date of Patent: Jul. 25, 2000

[54] FLOSSING TOOL

[76] Inventor: Brian K. Owens, 524 NW. First, Moore, Okla. 73160

[21] Appl. No.: 09/374,371

[22] Filed: Aug. 13, 1999

[51] Int. Cl.[7] .................................................. A61C 15/00
[52] U.S. Cl. ........................ 132/325; 132/323; 132/324
[58] Field of Search ................................ 132/325, 323, 132/324, 328, 326, 327, 321, 150; 15/167.1

[56] References Cited

U.S. PATENT DOCUMENTS

| | | | |
|---|---|---|---|
| 3,814,114 | 6/1974 | Roberts | 132/325 |
| 5,287,865 | 2/1994 | Fulton | 132/325 |
| 5,438,726 | 8/1995 | Leite | 132/325 |
| 5,816,271 | 10/1998 | Urso | 132/325 |

*Primary Examiner*—John J. Wilson
*Assistant Examiner*—Robyn K Doan
*Attorney, Agent, or Firm*—James T. Robinson

[57] ABSTRACT

A hand-held flossing tool provides a housing member having a spool housing integral therewith containing a replaceable spool of dental floss, a tension head consisting of two tension arms integrally molded to a yoke, each tension arm including a snap eye on one end and a gripping surface at the other end, and a stabilizer rotatably attached to the housing member. The dental floss strand, which passes from the housing through a spool housing slit and then through the snap eyes on the tension arms, is secured around a cleat on one of the tensions arms. The flosser places the stabilizer in the flosser's palm and holds the tension arm gripping surfaces between the flosser's thumb and index finger. The floss spool ratchets within the spool housing to permit adjustment of the tension on the strand of dental floss by rotation of a tension adjustment key extending through the bottom of the housing into the spool. A further adjustment of tension on the dental floss strand is provided as the flosser varies the force applied to the tension arm gripping elements. A removable cap on the spool housing permits replacement of a depleted dental floss spool. The cap is sealed to the top of the spool housing by a compression seal to prevent moisture from entering the spool housing. The tension adjustment key includes a barrier which resists entry of moisture and contaminants through the tension adjustment key access in the bottom of the spool housing.

16 Claims, 5 Drawing Sheets

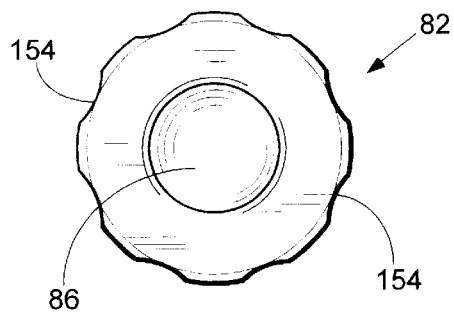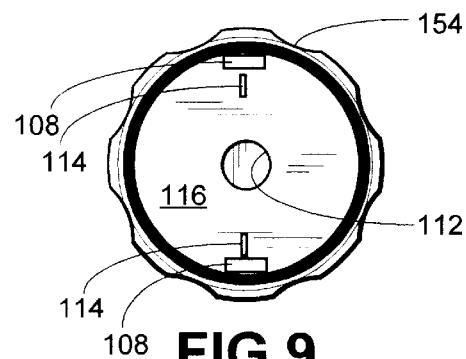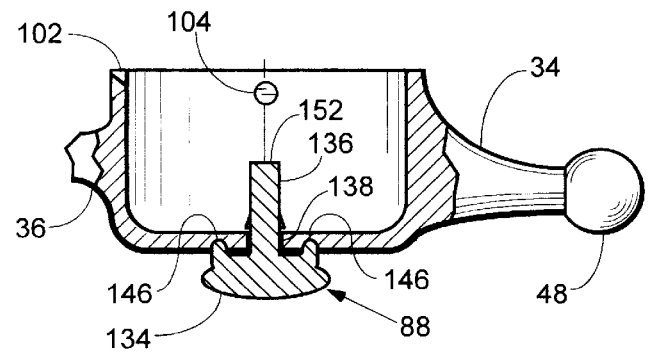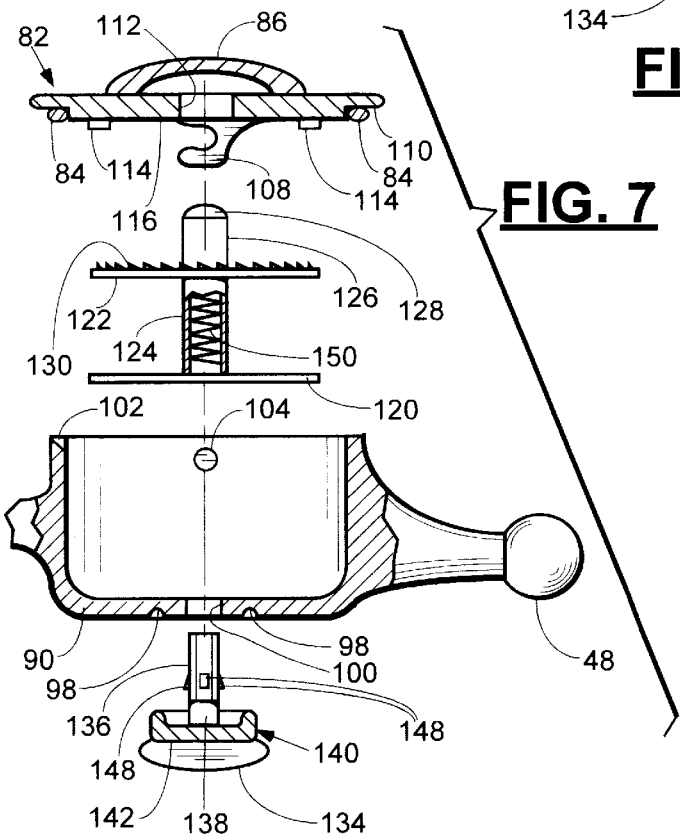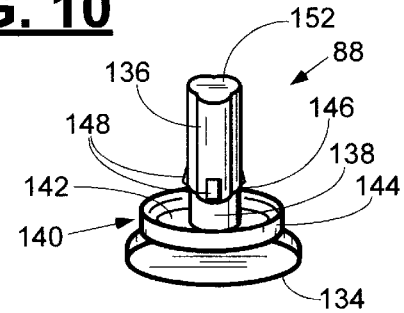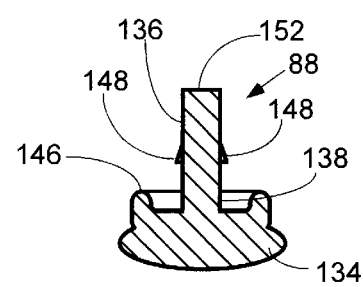

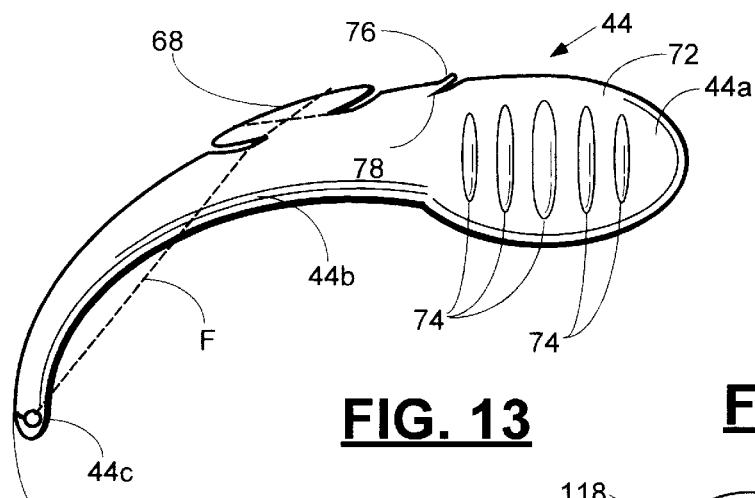
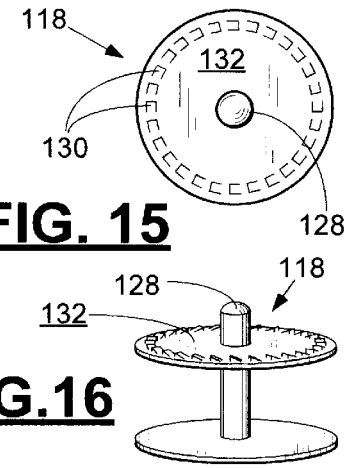
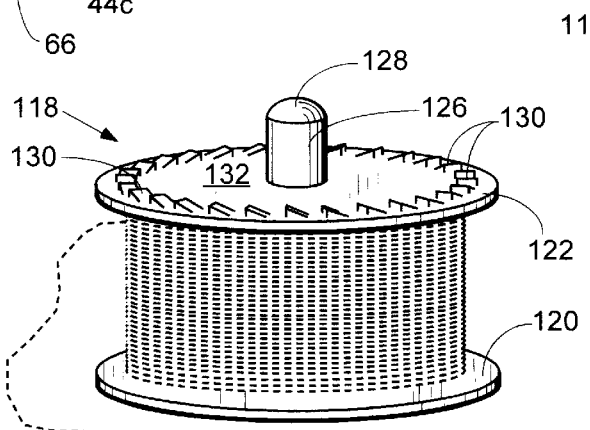
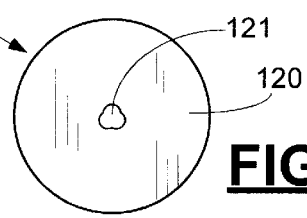
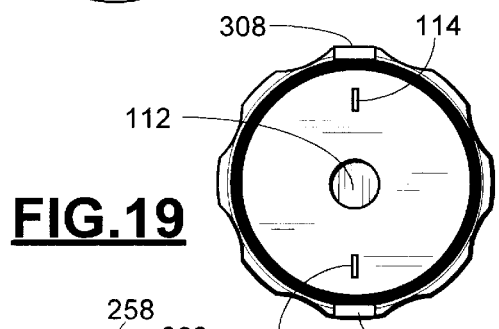
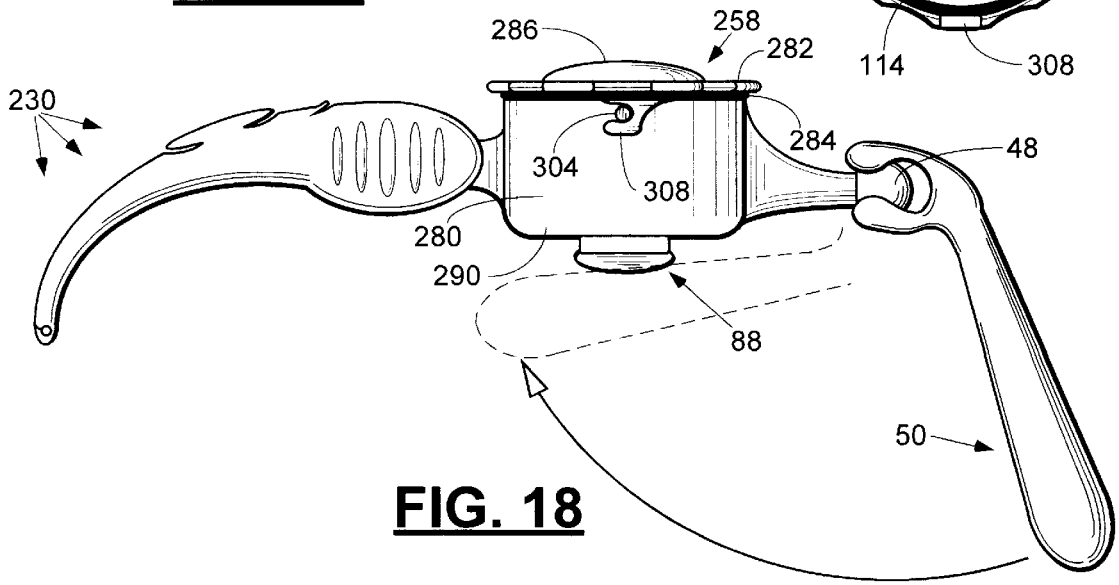

FLOSSING TOOL

BACKGROUND OF THE INVENTION

1. Field of the Invention

The present invention relates to a tool for use in conjunction with dental floss, and more particularly, but not by way of limitation, to a flossing tool which the flosser manipulates primarily by use of the flosser's thumb and index finger rather than wrist action.

2. Prior Art

U.S. Pat. No. 4,214,598, Lee, discloses a dental floss applicator which utilizes a single capstan to simultaneously advance the floss, generate floss tension, and hold the tension once generated. The capstan includes supply and take-up capstan portions.

U.S. Pat. No. 4,790,336, Kuo, is for a dental floss applicator which consists of a fork and a pair of elongated legs projecting from an elongated handle, a floss storage container positioned on the handle, and a reel on one side of the handle. Rotation of the reel withdraws a continuous string of ental floss under tension from the container and passes the dental floss from the container along the length of one leg, across the distance between the tips of the legs, along the length of the other leg, and onto a rotatable post on the underside of the handle.

U.S. Pat. No. 4,434,807, Huskey, is for a dental flossing aid. A supply of dental floss is mounted on an elongated member. Dental floss from the supply is threaded through a series of apertures in the elongated member. The apertures develop tension in the dental floss to resist the removal of floss from the floss supply. A pushkey assembly relieves tension in the dental floss so new floss can be withdrawn from the supply.

U.S. Pat. Des. No. 319,710, Lorenzana et al., is for an ornamental design for a dental floss tool.

U.S. Pat. No. 1,210,207, Roach, is for a dental floss holder. A supply of dental floss is contained within a tubular handle having an opening through which a strand of dental floss is drawn. The free end of the floss is wound about a yoke at the outer end of the tubular handle so that a small portion of the strand of dental floss can be placed within the operator's teeth without requiring the operator to insert fingers in the mouth.

U.S. Pat. No. 3,327,719, Ford, is for a dental floss holder with rotary floss tensioning means. A supply of dental floss, located within the handle portion, dispenses a strand of dental floss which is held taut across a pair of spaced arms for insertion into the spaces between the teeth.

The prior art includes a variety of dental floss holders which permit the operator (also referred to herein as "user" or "flosser") to insert a strand of dental floss into the flosser's mouth, but each device includes deficiencies. The flossing tool is manipulated by the flosser in the same manner as the flosser would manipulate a tooth brush, that is, by wrist and hand control. The small motor control required for precise manipulation of the dental floss between adjacent teeth is not achievable with wrist and hand control. Several of the prior art devices store soiled floss in close proximity to new floss, thereby promoting contamination of new floss by contact with soiled floss.

The prior art devices generally include a mechanism for providing tension on the strand of dental floss, but they do not permit adjustment of the tension. Greater tension is required for insertion of the dental floss between teeth which are touching or nearly touching, whereas lesser tension is required for insertion between teeth which have relatively larger spaces between them.

Finally, the prior art devices are, for the most part, disposable devices. That is, the flosser must dispose of the entire dental flossing tool and purchase a new tool containing new dental floss.

SUMMARY OF THE INVENTION

The present invention relates to a flossing tool for use in conjunction with dental floss. The flossing tool provides a housing member having a spool housing integral therewith containing a replaceable spool of dental floss, a tension head consisting of two tension arms integrally molded to a yoke, each tension arm including a snap eye on one end and a gripping surface at the other end, and a stabilizer rotatably attached to the housing member. The dental floss strand, which passes from the housing through a spool housing slit through floss guides (eyelets) and then through the snap eyes on the tension arms, is secured around a cleat on one of the tensions arms. The flosser places the stabilizer in the flosser's palm and holds the tension arm gripping surfaces between the flosser's thumb and index finger. The floss spool ratchets within the spool housing to permit adjustment of the tension on the strand of dental floss by rotation of a key extending through the bottom of the housing into a keyway in the spool. A further adjustment of tension on the dental floss strand is provided as the flosser varies the force applied to the tension arm gripping elements.

A removable cap on the spool housing permits replacement of a depleted dental floss spool. The cap is sealed to the top of the spool housing by a compression seal to prevent moisture from entering the spool housing. The key includes a barrier which resists entry of moisture and contaminants through the key access in the bottom of the spool housing.

One object of the present invention is to provide a flossing tool suitable for use with a spool of dental floss.

Another object of the present invention is to provide a flossing tool suitable for refilling with a new spool of dental floss when the old supply of dental floss is depleted.

Another object of the present invention is to minimize the risk of contamination of sterile dental floss by providing a spool housing which resists entry of moisture and contaminants.

Still another object of the present invention is to provide a flossing tool which includes a mechanism for adjusting the overall tension on the dental floss.

A still further object of the present invention is to provide a flossing tool which includes a further adjustment of the tension on the dental floss so the tension is automatically increased when the user attempts to insert the floss in tight crevices between closely-spaced teeth.

Yet another object of the invention is to provide a flossing tool which is manipulated primarily by the user's thumb and forefinger (also referred to herein as an index finger) rather than by the flosser's hand and wrist.

Yet another object of the invention is to provide a flossing tool which includes a stabilizer to be held firmly in the flosser's palm while the user grasps the tension arms of the flossing tool between the user's thumb and forefinger.

Yet another object of the invention is to provide a flossing tool which permits rotation of the floss-bearing portion of the tool for flossing the flosser's upper teeth while the stabilizer remains held firmly in the flosser's palm.

Yet another object of the invention is to provide a flossing tool stabilizer which includes an exterior layer of thermoplastic elastomer.

Another object of the invention is to provide a flossing tool which can be refilled with new dental floss.

Another object of the invention is to provide a flossing tool which folds into a compact unit for storage.

Other objects, features, and advantages of the present invention will become clear from the following description of the preferred embodiment when read in conjunction with the accompanying drawings and claims.

BRIEF DESCRIPTION OF THE DRAWINGS

FIG. 7 is an exploded view of the spool housing, the floss spool, the spool housing cap, and the tension adjustment key of the flossing tool of FIGS. 1–4, with the spool housing partially cut away.

FIG. 8 is a view of the top of the spool housing cap of the flossing tool of FIGS. 1–4.

FIG. 9 is a view of the bottom of the spool housing cap of the flossing tool of FIGS. 1–4.

FIG. 10 is a partial cross-sectional view showing the tension adjustment key and the spool housing of the flossing tool of FIGS. 1–4.

FIG. 11 is an isometric view of the tension adjustment key shown in FIGS. 7 and 10.

FIG. 12 is a cross-sectional view of the tension adjustment key shown in FIGS. 7, 10, and 11.

FIG. 13 is a detail of the left tension arm of the flossing tool shown in FIGS. 1–4.

FIG. 14 is an isometric view of the floss spool shown in FIGS. 4 and 7.

FIG. 15 is a top view of the floss spool shown in FIGS. 4, 7, and 14.

FIG. 16 is an isometric view of the floss spool shown in FIGS. 4, 7, and 14–15.

FIG. 17 is a bottom view of the floss spool shown in FIGS. 4, 7, and 14–16.

FIG. 18 is a pictorial view of an alternate embodiment of the flossing tool of the present invention.

FIG. 19 is a view of the bottom of the spool housing cap of the flossing tool shown in FIG. 18.

DETAILED DESCRIPTION OF THE INVENTION

In the following description of the invention, like numerals and characters designate like elements throughout the figures of the drawings.

Figure 1:
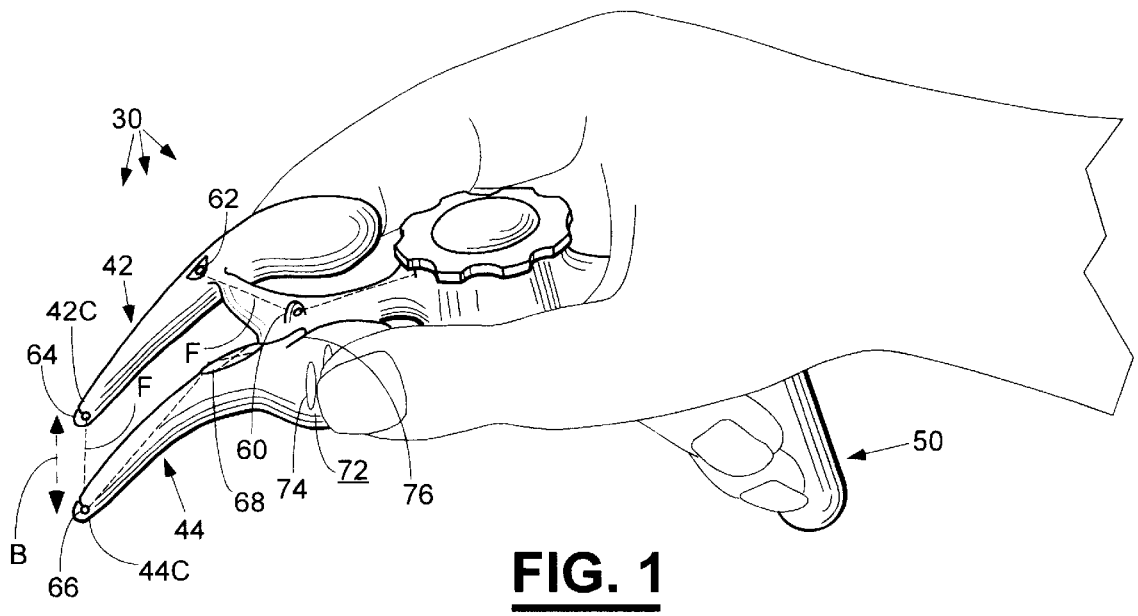
FIG. 1 is a pictorial of the flossing tool of the present invention showing the flossing tool in the hand of a flosser.
Figure 2:
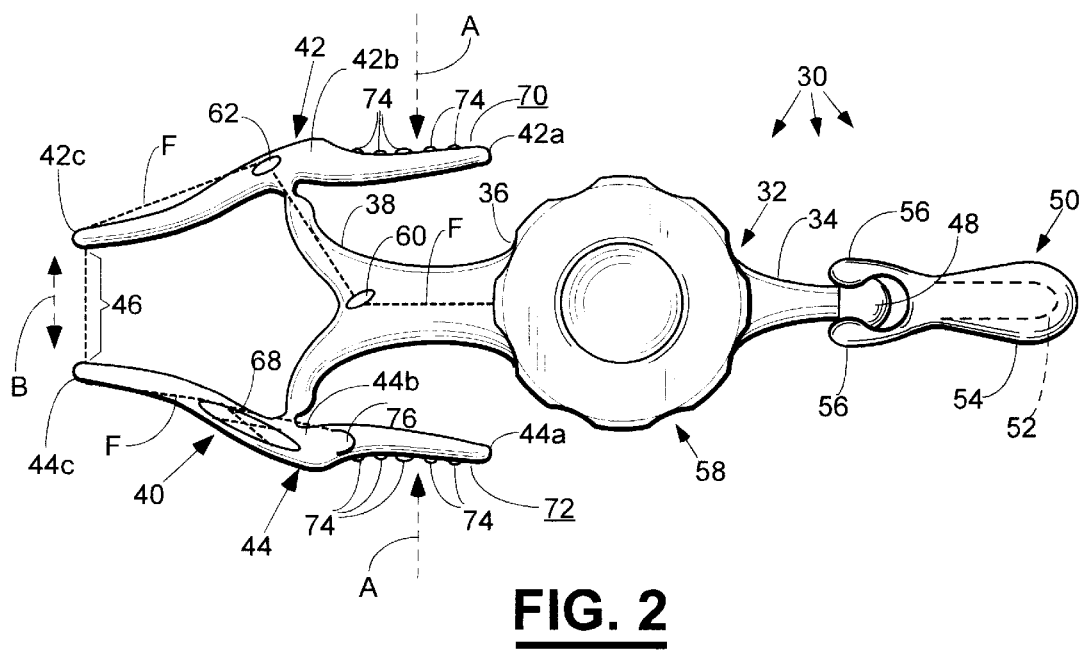
FIG. 2 is a top view of the flossing tool shown in FIG. 1.
Figure 3:
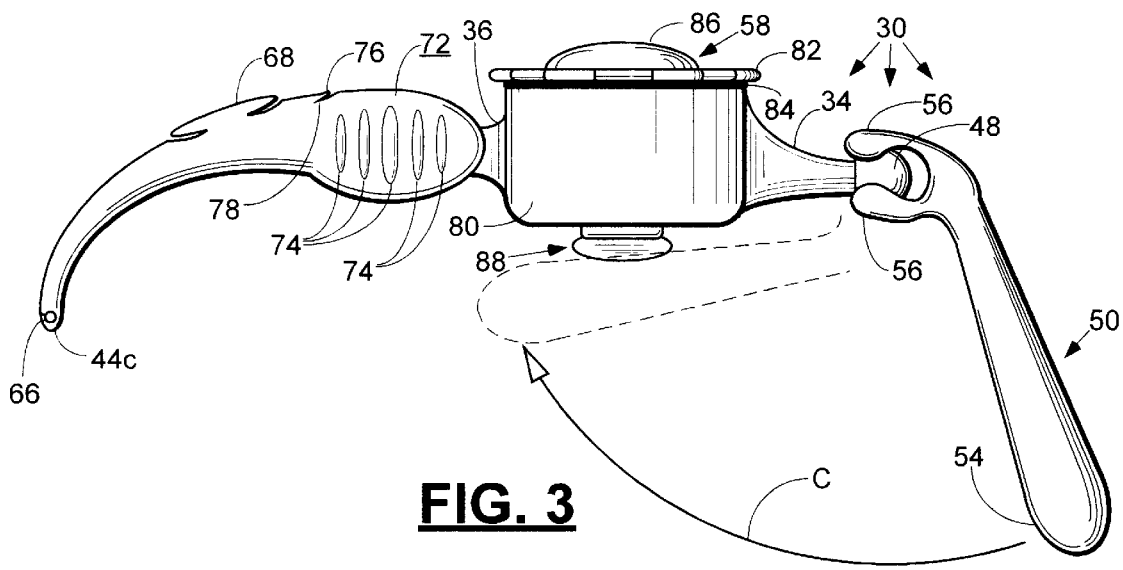
FIG. 3 is an elevational view of the flossing tool shown in FIG. 1.

Referring generally to FIGS. 1–3, a hand-held flossing tool 30 includes a housing member 32 and a stabilizer 50. The housing member 32 has a proximate end 34, a middle portion 36, and a distal end 38. A tension head 40 is integrally molded to the housing member 32 at the distal end 38. The tension head 40 is formed by a right tension arm 42 and a left tension arm 44 having, respectively, a gripping end 42a, 44a, a floss-bearing end 42c, 44c, and an intermediate portion 42b, 44b. The floss-bearing ends 42c, 44c define a flossing gap 46.

At the proximate end 34 of the housing member 32, an integral ball 48 permits attachment of the stabilizer 50. The stabilizer 50 includes a core 52 of hard plastic to which an exterior thermoplastic elastomer layer 54 has been molded. Spring ears 56 (see FIG. 21) on the stabilizer 50 spread slightly to receive the ball 48.

Thermoplastic elastomers (TPEs), which are well known, are based on several different polymer and polymer blend types which provide rubber-like (elastomer) properties in a material than can be processed on conventional thermoplastic processing equipment. In performance, TPEs provide good elastic recovery, compression set and low temperature flexibility. These physical properties are provided in a material that is processable at elevated temperature and can be reheated and reprocessed as any thermoplastic material.

In FIGS. 1–3, the flossing tool 30 is shown in a position for flossing lower teeth. Because the stabilizer 50 is attached to the integral ball 48 by spring ears 56, the stabilizer 50 can move from the position shown in FIGS. 1–3 along C to the folded position indicated by dashed lines in FIG. 3. The housing member 32 can rotate 180 degrees with respect to the stabilizer 50 so that the left tension arm 44 is grasped by the user's right forefinger and the right tension arm 42 is grasped by the user's right thumb. In this position, the floss-bearing ends 42c and 44c and the flossing gap defined thereby are directed upwardly for flossing upper teeth.

Still referring to FIGS. 1–3, dental floss F from a floss dispenser 58 integrally molded in the middle portion 36 of the housing member 32 is threaded through eyelets 60 and 62, then through snap eyes 64 and 66, and tied off around a cleat 68. See FIG. 20 for a detailed structure of the snap eyes 64 and 66. Each gripping end 42a, 44a of the tension arms 42 and 44, respectively, includes gripping surfaces 70, 72, respectively, to which spaced thermoplastic elastomer strips 74 are molded.

It will be understood to one skilled in the art that the snap eyes 64, 66 could be replaced by eyelets and, likewise, snap eyes could be substituted for the eyelets 60, 62. In the presently preferred embodiment, snap eyes 64, 66 are used in the floss-bearing ends 42c and 44c of the right tension arm 42 and the left tension arm 44, respectively, because soiled floss (following use) is most easily removed by snapping the floss out of the snap eyes 64, 66 and thereby avoiding contamination of additional portions of the flossing tool 30. This concern for sanitation is especially important with respect to the snap eye 66 located in the floss-bearing end 44c of the left tension arm 44. Removal of the used floss F is most easily accomplished by unwrapping the loose end of the floss F from the cleat 68 and then pulling the floss F from the snap eye 66. At this juncture, clean floss can be released from the floss dispenser 58. The used floss is discarded, new (clean) floss is snapped into place in the snap eye 66, and the loose end of the floss is tied off around the cleat 68. Any extra length of floss is cut off using the floss cutter 76 and discarded.

Still referring to FIGS. 1–3, the flosser holds the flossing tool (FIG. 1) with thumb and forefinger on the gripping surfaces 72 and 70 of tension arms 44 and 42, respectively. The stabilizer 50 rests within the confines of the flosser's remaining fingers. Application of pressure (by thumb and forefinger) along A against the gripping surfaces 70, 72 of the tension arms 42, 44 causes the flossing-bearing ends 42c, 44c of the tension arms 42, 44 to move apart along B and increases the tension on the floss F located in the flossing gap 46.

Figure 4:
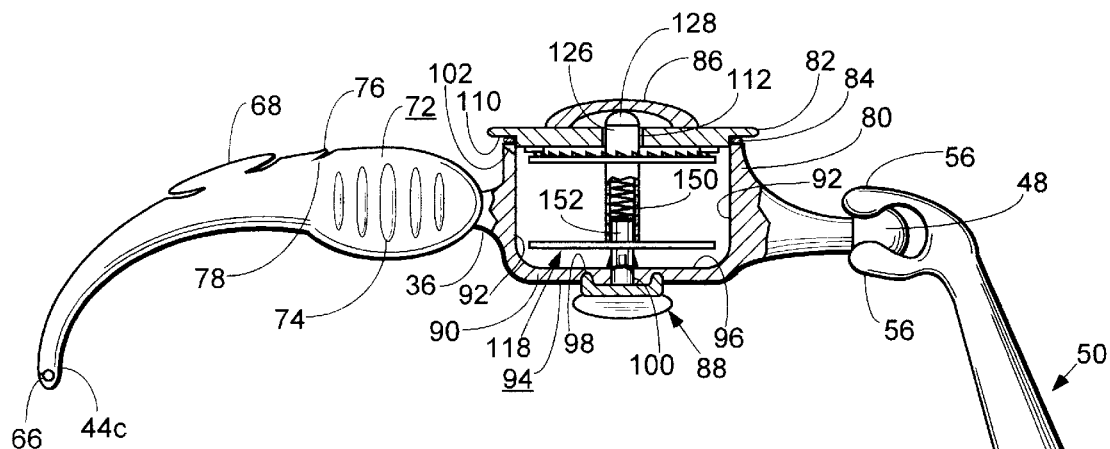
FIG. 4 is a partial cross section of the flossing tool shown in FIG. 3.

A floss cutter 76 permits the flosser to cut off previously used floss (not shown). The floss cutter 76 is shown in FIGS. 3 and 4 as a crevice 78 molded into the left tension arm 44. The flosser pulls the floss F into the molded crevice 78 and, by continuing to pull on the floss F after the floss F is wedged into the molded crevice 78, breaks the floss. It will be understood by one skilled in the art that a cutter (not shown) such as a small segment of a razor blade could be molded into the left tension arm 44 at the location of the crevice 78. The floss F is drawn from the floss dispenser 58 through a floss slit 102.

Referring now to FIGS. 3 and 4, the floss dispenser 58 includes a spool housing 80, a spool housing cap 82, a spool housing seal 84, a flexible tension release cover 86, and a tension adjustment key 88. As shown in FIG. 4, the flexible tension release cover 86 is molded to the spool housing cap 82.

As shown in FIG. 4, the spool housing 80 includes a spool housing bottom 90 and a spool housing cylindrical sidewall 92. The spool housing bottom 90 has an exterior surface 94, an interior surface 96, a tension adjustment key mating groove 98, and a tension adjustment key bore 100. The tension adjustment key mating groove 98 is shown in detail in FIGS. 6A and 7. The tension adjustment key bore 100 is shown more clearly in FIGS. 5, 6A, and 7.

Figures 5, 6, 6A:
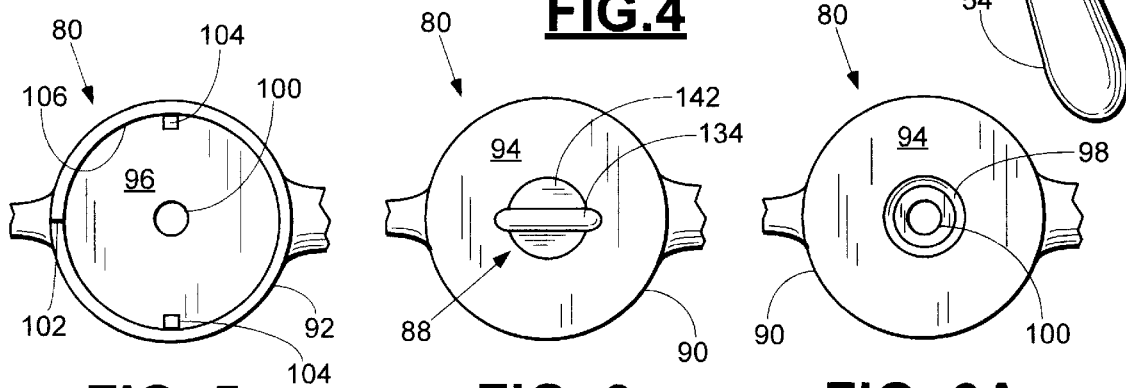
FIG. 5 is a top view of the spool housing portion of the flossing tool of FIGS. 1–4 with the cap removed.
FIG. 6 is a bottom view of the spool housing of the flossing tool of FIGS. 1–4 with the tension adjustment key in place.
FIG. 6A is a bottom view of the spool housing of the flossing tool of FIGS. 1–4 with the tension adjustment key removed.

Referring now to FIG. 4 in conjunction with FIG. 5, the floss slit 102 (see FIG. 1) in the spool housing cylindrical sidewall 92 provides a through which the floss F passes from the interior of the spool housing 92 to the eyelet 60 (see FIG. 1). Interior studs 104 located on the interior surface 106 of the spool housing cylindrical sidewall 92 mate with interior locking ears 108 attached to the spool housing cap 82 (see FIG. 7).

Referring now to FIG. 4 in conjunction with FIGS. 7, 8, and 9, the spool housing cap 82 includes a spool housing cap sealing surface 110, a spool housing cap bore 112, and ratchet ears 114 on the interior surface 116 of the spool housing cap 82. In the presently preferred embodiment, the ratchet ears 114 and the interior locking ears 108 are molded as one piece with the spool housing cap 82.

Still referring to FIG. 4, a floss spool 118 is disposed within the spool housing 80. As detailed in FIGS. 7, 14, 15, and 16, the floss spool 118 is formed by parallel lower and upper plates 120 and 122, respectively, mounted on a hollow axle 124. The hollow axle 124 extends upwardly from the upper plate 122 to form an extended axle portion 126 having a rounded end 128. Ratchet teeth 130 are spaced about the circumference of the outer surface 132 of the upper plate 122.

Referring now to FIG. 4 in conjunction with FIGS. 6, 7, 10, 11, and 12, the tension adjustment key 88 includes a grip portion 134 connected to a trilobular blade portion 136 by a cylindrical neck portion 138. The cylindrical neck portion 138 has a diameter which is equal to the greatest dimension across the trilobular blade portion 136. The trilobular blade portion 136 is thus able to pass through the tension adjustment key bore 100, and the cylindrical neck portion 138 is snugly but movably disposed within the tension adjustment bore 100. A sealing dish 140 formed by a sealing dish plate 142 and a sealing dish cylindrical sidewall 144. The sealing dish plate 142 is perpendicular to a plane formed generally along the grip portion 134 with edges 146 of the sealing dish cylindrical sidewall 144 extending toward the trilobular blade portion 136. A compressible retainer 148 is located on each lobe of the trilobular blade portion 136 adjacent the cylindrical neck portion 138. When the tension adjustment key 88 is inserted through the tension adjustment key bore 100 (see FIG. 7), the compressible retainers 148 spring outwardly above the interior surface 96 of the spool housing bottom 90 to prevent removal of the tension adjustment key 88 from the spool housing bottom 90. In this position, the cylindrical neck portion 138 is disposed within the tension key adjustment bore 100 and supported by the spool housing bottom 90.

FIG. 17 shows a bottom view of the lower plate 120 of the floss spool 118. A center trilobular aperture 121 mates with the trilobular blade portion 136 of the tension adjustment key 88 so that rotation of the tension adjustment key 88 causes the floss spool 118 to rotate correspondingly.

Referring again to FIG. 4, a spring 150 disposed within the hollow axle 124 of the floss spool 118 is compressedly biased against the end 152 of the trilobular blade portion 136 of the tension adjustment key 88.

Referring now to FIG. 5, a top view of the spool housing 80 (with the spool housing cap 82 removed) shows the spool housing cylindrical sidewall 92, the spool housing bottom interior surface 96, the tension adjustment key bore 100, the floss slit 102 in the spool housing cylindrical sidewall 92, and the interior studs 104 located on the interior surface 106 of the spool housing cylindrical sidewall.

In FIG. 6, the tension adjustment key 88 is shown after it is inserted into the tension adjustment key bore 100 in the spool housing bottom 90. The grip portion 134 of the tension adjustment key 88 and the sealing dish plate 142 are shown against the spool housing bottom exterior surface 94. In FIG. 6A, a view of the spool housing bottom 90 shows the tension adjustment key mating groove 98 concentric to the tension adjustment key bore 100.

FIG. 7 illustrates assembly of the floss spool 118, the spool housing 80, the spool housing cap 82, the tension adjustment key 88, and the spring 150.

First, the tension adjustment key 88 is inserted through the tension adjustment key bore 100 in the spool housing bottom 90 until the compressible retainers 148 spring outwardly from the trilobular blade portion 136 of the tension adjustment key 88. The sealing dish cylindrical sidewall edges 146 are disposed in the tension adjustment key mating groove 98 (FIG. 10). When the sealing dish cylindrical sidewall edge 146 is disposed within the tension adjustment key mating groove 98, a water-resistant enclosure is formed. That is, water can enter the interior of the spool housing 80 only by traveling around the sealing dish cylindrical sidewall edges 146, along the sealing dish plate 142, and between the cylindrical neck portion 138 and the tension adjustment key bore 100. In FIG. 10, the spool housing 80 is cut away to show the tension adjustment key 88 following installation in the spool housing bottom 90 of the spool housing 80. The trilobular blade portion 136 of the tension adjustment key 88 extends upwardly from the spool housing bottom interior surface 96 and is held in place by the compressible retainers 148.

The tension adjustment key 88 is thus supported by the spool housing bottom 90 of the spool housing 80 by virtue of the location of the cylindrical neck portion 138 of the tension adjustment key 88 within the tension key adjustment bore 100. Once the tension adjustment key 88 is inserted through the tension adjustment key bore 100, the compressible retainers 148 firmly secure the tension adjustment key 88 firmly to the spool housing bottom 90.

Following installation of the adjustment key 88, the spring 150 is placed within the hollow axle 124 of the floss spool 118. The floss spool 118 (with the spring 150 in place) is then placed downwardly over the trilobular blade portion 136 of the tension adjustment key 88. It will be understood to one skilled in the art that the present invention contemplates use of preloaded floss spools. Thus, following installation of the floss spool 118 as discussed above, the loose end of the floss F would be directed through the floss slit 102 (FIGS. 1, 4, 5, 7, and 10) for threading through eyelets 60, 62 and snap eyes 64, 66.

Referring still to FIG. 7 in conjunction with FIG. 4, the spool housing cap 82, with the spool housing seal 84 in place, is placed over the extended axle portion 126 so the extended axle portion 126 is received by and extends upwardly through the spool housing cap bore 112. The spool housing cap 82 is forced downwardly against the spool housing seal 84 and, with the interior locking ears 108 aligned with the interior studs 104 located on the interior surface 106 of the spool housing cylindrical sidewall 92, the spool housing cap 82 is twisted in clockwise fashion until the interior locking ears 108 engage the interior studs 104.

Referring now to FIG. 4, with the spool housing cap 82 in place, the floss spool 118 is forced upwardly by the spring 150, thereby causing two of the ratchet teeth 130 (located on the top plate 122 of the floss spool) to engage the ratchet ears 114 located on the bottom surface of the spool housing cap 82. The rounded end 128 of the extended axle portion 126 of the hollow axle 124 is in contact with the flexible tension release cover 86. The flosser can now rewind the floss F onto the floss spool 118 by twisting the grip portion 134 of the tension adjustment key 88 in a clockwise direction (as the flosser views the bottom surface 94 of the spool housing 90). As the tension adjustment key 88 is twisted in a clockwise direction, the spring 150 is compressed and the floss spool 118 moves downwardly to permit the ratchet teeth 130 to slide past the ratchet ears 114.

Referring now to FIG. 2, the loose end of the floss F is threaded through eyelets 60 and 62, then through snap eyes 64 and 66, and tied off around the cleat 68. To increase tension on the floss F, the flosser merely twists the grip portion 134 of the tension adjustment key 88 in a clockwise direction.

To dispense additional floss following use of the previously dispensed floss, the flosser removes the loose end of the floss F from the cutter 76/78 and then unwraps the floss from the cleat 68. The user removes the previously used floss portion located in the floss gap 46 (FIG. 2) from the snap eye 66 and releases new floss by pressing the flexible tension release cover 86, thereby causing the floss spool 118 to move downwardly. While continuing to depress the flexible tension release cover 86, the flosser pulls out a length of new floss and releases the flexible tension release cover 86, thereby permitting the floss spool 118 to return to its normal position. The flosser then snaps the new length of floss into the snap eye 66 and ties the remaining new floss around the cleat 68. As a last step, the user places the loose end of the floss F in the cutter 76/78 and cuts off the excess floss. With a new strand of floss F in place, the flosser adjusts the tension as previously described and is ready to floss.

Referring now to FIG. 8, the spool housing cap 82 includes circumferential finger depressions 154 to assist the flosser in removal and replacement of the spool housing cap 82.

FIG. 13 provides a detailed view of the left tension arm 44, the gripping end 44a, the intermediate portion 44b, the floss-bearing end 44c, the snap eye 66, the cleat 68, the gripping surface 72, the thermoplastic elastomer strips 74, and the floss cutter 76.

FIGS. 18 and 19 illustrate an alternate embodiment of flossing tool of the present invention. A hand-held flossing tool 230 includes a floss dispenser 258 having a spool housing 280, a spool housing cap 282, a spool housing seal 284, and a flexible tension release cover 286. Exterior locking ears 308 attached to the spool housing cap 282 engage exterior studs 304 attached to the exterior surface of the spool housing cylindrical sidewall 292. The hand-held flossing tool 230 is like the hand-held flossing tool of FIGS. 1–4 with respect to the tension head 40, the stabilizer 50, the tension adjustment key 88, and the floss spool 118.

Figure 20:
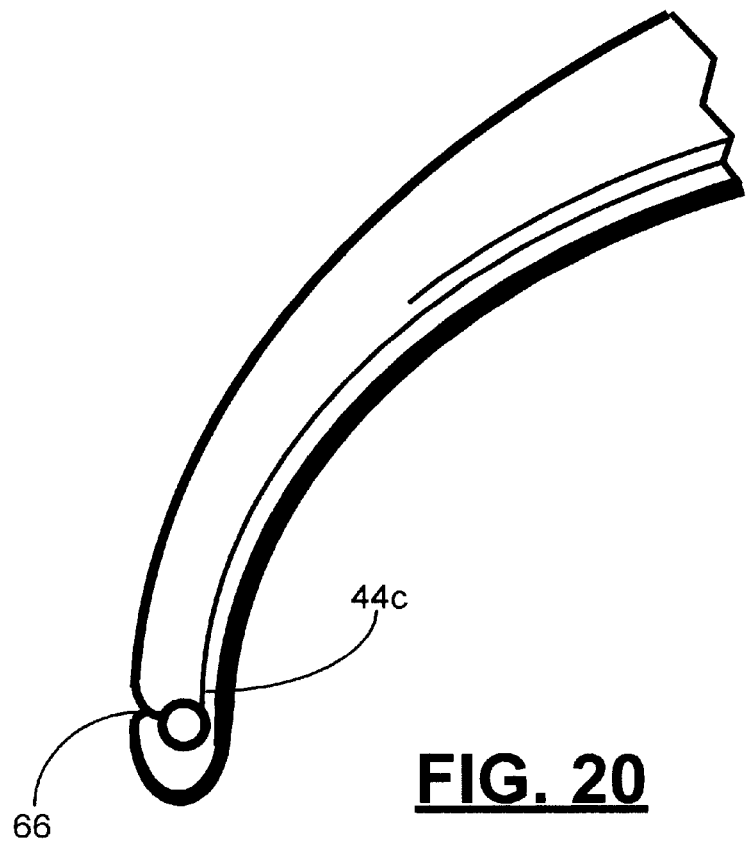
FIG. 20 is an enlarged view of a tip of a tension arm of the present invention showing the snap eye.

FIG. 20 is a greatly enlarged detail of the snap eye 66 of the left tension arm 44. It will be understood to one skilled in the art that the floss guides can be either eyelets (like 60 and 62) or snap eyes (like 64 and 66). The use of snap eyes 64 and 66 in the present invention permits removal of soiled (i.e., used) floss while avoiding threading used floss either eyelets or snap eyes. The removal and disposal of soiled floss helps to keep the remaining floss sanitary.

Figure 21:
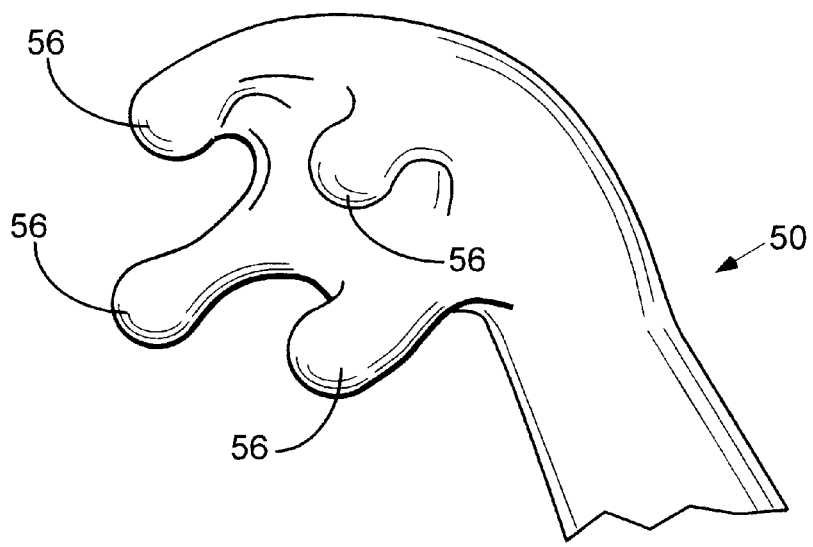
FIG. 21 is an enlarged view of the socket portion of the stabilizer bar of the present invention.

FIG. 21 is a greatly enlarged view of the stabilizer 50 and the spring ears 56 of the present invention.

In the presently preferred embodiment of the hand-held flossing tool of the present invention, the housing member 32, the tension head 40, and the stabilizer core 52 (including the integral ball 48) are molded from a suitable hard plastic. As discussed above, the exterior thermoplastic elastomer layer 54 of the stabilizer 50 and the spaced thermoplastic elastomer strips 74 are constructed from materials well known in the art. Likewise, the hard plastic suitable for the housing member 32 (including the spool housing 80), the spool housing cap 82, the tension head 40, and the stabilizer core 52 can be formed of any thermoplastic, or any thermosetting plastic such as, without limitation, ABS, PC, PC/ABS, Valox, Rynite, LCP, polyethylene, and PVC.

Whereas the present invention has been described in relation to the drawings attached hereto, it should be understood that other and further modifications, apart from those shown or suggested herein, may be made within the spirit and scope of this invention.

What is claimed is:

1. A hand-held flossing tool for use with dental floss, comprising:

a housing member having a distal end, a proximate end, and a middle portion, said housing member including an integrally molded tension head at said distal end, said tension head further comprising a left tension arm and a right tension arm defining a flossing gap therebetween, and an integrally molded ball at said proximate end, said housing member further including a floss dispenser in said middle portion of said housing member, so that floss from said floss dispenser is stretched taut across said flossing gap;

a stabilizer rotatably attached to said integrally molded ball located at said proximate end of said housing member, wherein the flosser grasps said tension arms between the flosser's thumb and index finger while curling the flosser's remaining fingers about said stabilizer, so that the floss in said flossing gap is directed by the movement of the flosser's thumb and index finger to the flosser's teeth;

guide means for guiding said floss along said right tension arm, across said flossing gap, and across said left tension arm; and tiedown means for securing the loose end of said floss.

2. The hand-held flossing tool of claim 1 wherein said stabilizer comprises a core of hard plastic and an exterior thermoplastic elastomer layer, said stabilizer terminating at one end in at least three spring ears, said spring ears spaced to flexibly receive and retain said integrally molded ball located at said proximate end of said housing member.

3. The hand-held flossing tool of claim 1 wherein each said tension arm has a gripping end, a floss-bearing end, and an intermediate portion, wherein each said tension arm is flexibly molded to said distal end of said housing member at an attachment point located in said intermediate portion of said tension arm, and, further, wherein each said tension arm gripping end includes a gripping surface opposite said housing member, so that, when the flosser exerts a force against said gripping surfaces of said tension arms, said floss-bearing ends of said tension arms move outwardly with respect to one another and thereby place additional tension on said floss located in said flossing gap.

4. The hand-held flossing tool of claim 3 wherein said gripping surfaces include spaced strips of thermoplastic elastomer molded thereto.

5. The hand-held flossing tool of claim 1 wherein said guide means comprises a plurality of eyelets.

6. The hand-held flossing tool of claim 1 wherein said guide means comprises a plurality of snap eyes.

7. The hand-held flossing tool of claim 1 wherein said guide means comprises at least one eyelet and at least one snap eye.

8. The hand-held flossing tool of claim 1 wherein said tiedown means comprises a cleat attached to said left tension arm.

9. The device of claim 1 further comprising a floss cutter molded into said left tension arm, said floss cutter comprising a narrow channel into which said floss is wedged for cutting.

10. The device of claim 1, wherein said floss dispenser further comprises:
- a spool housing integrally molded in said middle portion of said housing member, said spool housing being characterized as having a spool housing bottom, a spool housing cylindrical sidewall, a spool housing bottom exterior surface, and a spool housing bottom interior surface, said spool housing further comprising:
  - a floss slit in said spool housing cylindrical sidewall adjacent said distal end of said housing member;
  - integrally molded diametrically opposed interior studs located on the interior of said spool housing cylindrical sidewall;
  - a tension key adjustment bore centrally located in said spool housing bottom; and
  - said spool housing bottom exterior surface having a tension adjustment key mating groove concentric to said tension adjustment key bore;
- a spool housing cap, said spool housing cap being characterized as having a spool housing cap interior surface, a centrally located spool housing cap bore, a spool housing cap sealing surface along the circumference of said spool housing cap interior surface, at least two interior diametrically opposed locking ears integrally molded with said spool housing cap, said interior locking ears extending perpendicularly from the plane of said spool housing cap interior surface, and at least two diametrically opposed ratchet ears, said ratchet ears being located immediately adjacent said interior locking ears and between said interior locking ears and said spool housing cap bore;
- a spool housing seal positioned along said spool housing cap sealing surface to form a seal between said spool housing cap and said spool housing when said interior locking ears engage said integrally molded diametrically opposed interior studs located on the interior of said spool housing cylindrical sidewall;
- a floss spool for supplying dental floss through said floss slit in said spool housing cylindrical sidewall adjacent said distal end of said housing member to said integrally molded tension head, said floss spool comprising:
  - a floss spool lower plate having a central trilobular aperture therein;
  - a floss spool upper plate having an outer surface;
  - a hollow axle connecting said floss spool lower plate and said floss spool upper plate, said hollow axle extending upwardly from said upper plate to form an extended axle portion having a rounded end, said hollow axle's other end terminating at said central trilobular aperture in said floss spool lower plate; and
  - ratchet teeth spaced about the circumference of said outer surface of said floss spool upper plate; and
- tension adjustment means for adjusting the tension on said dental floss, said tension adjustment means comprising:
  - a tension adjustment key extending upwardly through said tension adjustment key bore in said spool housing bottom, said tension adjustment key being characterized as having a grip portion, a trilobular blade portion mating with said trilobular aperture in said floss spool lower plate, a cylindrical neck portion mating with said tension adjustment key bore, a compressible retainer located on each lobe of said trilobular blade portion, so that, when said tension adjustment key is inserted in said tension adjustment key bore in said spool housing bottom from said spool housing bottom exterior surface, through said spool housing bottom and through said spool housing bottom interior surface, said compressible retainers first compress to permit insertion of said tension adjustment key in said tension adjustment key bore and then spring outwardly above said interior surface of said spool housing bottom to prevent removal of said tension adjustment key from said spool housing bottom, said tension adjustment key further comprising a sealing dish, said sealing dish further comprising a sealing dish plate extending outwardly perpendicular to said cylindrical neck portion and said trilobular blade portion and a sealing dish cylindrical sidewall extending from said grip portion toward said cylindrical neck portion, said sealing dish cylindrical sidewall being characterized as having a sealing dish cylindrical sidewall edge mating with said tension adjustment key mating groove; and
  - a spring disposed within said hollow axle of said floss spool, one end of said spring terminating at said rounded end of said extended axle portion and the other end of said spring terminating at said trilobular blade portion of said tension adjustment key;
- wherein said spring biasingly engages said ratchet teeth on said outer surface of said floss spool upper plate with said diametrically opposed ratchet ears located immediately adjacent said interior locking ears extending perpendicularly from the plane of said spool housing cap interior surface and, further, wherein pressure applied against said rounded end of said extended axle portion through said flexible tension release cover depresses said floss spool against said spring and disengages said ratchet teeth from said ratchet ears to permit withdrawal of new floss; and wherein clockwise rotation of said tension adjustment key when said ratchet teeth are engaged with said ratchet ears results in a stepwise increase in the tension on said floss.

11. The device of claim 10, wherein said spool housing cap further comprises finger depressions about the circumference of said spool housing cap to facilitate ease of removal and replacement of said spool housing cap.

12. The device of claim 10, wherein said spool housing seal is an O-ring.

13. The device of claim 10, wherein said spool housing seal is a compressible rubber gasket.

14. The device of claim 10, wherein said floss spool is preloaded with dental floss.

15. The device of claim 1, wherein all corners and edges of said device are rounded to prevent abrasion of the flosser's mouth.

16. The hand-held flossing tool of claim 1 wherein said stabilizer includes four spring ears spaced to flexibly receive and retain said integrally molded ball located at said proximate end of said housing member.

* * * * *